United States Patent [19]
Virnich et al.

[11] Patent Number: 5,810,846
[45] Date of Patent: Sep. 22, 1998

[54] VASCULAR HOLE CLOSURE

[75] Inventors: Patrick E. Virnich, Norwalk; Salvatore Castro, Seymour; Dragomir C. Marinkovich, Sandy Hook, all of Conn.

[73] Assignee: United States Surgical Corporation, Norwalk, Conn.

[21] Appl. No.: 510,834

[22] Filed: Aug. 3, 1995

[51] Int. Cl.⁶ .................................................. A61B 17/10
[52] U.S. Cl. ........................... 606/142; 606/139; 227/901
[58] Field of Search ................................... 606/143, 138, 606/142, 139, 148, 151, 140, 141; 227/901, 175.1–182

[56] References Cited

U.S. PATENT DOCUMENTS

| | | |
|---|---|---|
| Re. 34,866 | 2/1995 | Kensey et ao. . |
| 2,513,771 | 7/1950 | Williams . |
| 3,575,038 | 4/1971 | Mallett ..................................... 128/322 |
| 4,086,926 | 5/1978 | Green et al. ............................. 128/334 |
| 4,532,134 | 7/1985 | Malette et al. . |
| 4,744,364 | 5/1988 | Kensey . |
| 4,771,782 | 9/1988 | Millar . |
| 4,852,568 | 8/1989 | Kensey . |
| 4,854,320 | 8/1989 | Dew et al. . |
| 4,890,612 | 1/1990 | Kensey . |
| 4,929,340 | 5/1990 | Kirsch et al. . |
| 5,021,059 | 6/1991 | Kensey et al. . |
| 5,030,226 | 7/1991 | Green et al. . |
| 5,053,046 | 10/1991 | Janese . |
| 5,061,274 | 10/1991 | Kensey . |
| 5,100,420 | 3/1992 | Green et al. ............................. 606/143 |
| 5,108,420 | 4/1992 | Marks . |
| 5,108,421 | 4/1992 | Fowler . |
| 5,116,357 | 5/1992 | Eberbach . |
| 5,122,155 | 6/1992 | Eberbach . |
| 5,129,882 | 7/1992 | Weldon et al. . |
| 5,141,515 | 8/1992 | Eberbach . |
| 5,147,373 | 9/1992 | Ferzli . |
| 5,156,613 | 10/1992 | Sawyer . |
| 5,192,300 | 3/1993 | Fowler . |
| 5,192,301 | 3/1993 | Kamiya et al. . |
| 5,192,302 | 3/1993 | Kensey et al. . |
| 5,207,670 | 5/1993 | Sinofsky . |
| 5,207,691 | 5/1993 | Nardella . |
| 5,221,259 | 6/1993 | Weldon et al. . |
| 5,222,974 | 6/1993 | Kensey et al. . |
| 5,246,441 | 9/1993 | Ross et al. . |
| 5,254,105 | 10/1993 | Haaga . |
| 5,275,616 | 1/1994 | Fowler . |
| 5,282,827 | 2/1994 | Kensey et al. . |
| 5,290,310 | 3/1994 | Makower et al. . |
| 5,292,332 | 3/1994 | Lee . |
| 5,310,407 | 5/1994 | Casale . |
| 5,312,435 | 5/1994 | Nash et al. . |
| 5,320,639 | 6/1994 | Rudnick . |
| 5,324,306 | 6/1994 | Makower et al. ....................... 606/213 |
| 5,326,350 | 7/1994 | Li . |
| 5,330,446 | 7/1994 | Weldon et al. . |
| 5,334,216 | 8/1994 | Vidal et al. . |
| 5,334,217 | 8/1994 | Das . |
| 5,342,393 | 8/1994 | Stack . |
| 5,342,394 | 8/1994 | Matsuno et al. . |
| 5,350,399 | 9/1994 | Erlebacher et al. . |

(List continued on next page.)

FOREIGN PATENT DOCUMENTS

| | | |
|---|---|---|
| 0637431 | 2/1995 | European Pat. Off. . |
| 0656191 | 6/1995 | European Pat. Off. . |
| WO9222252 | 12/1992 | WIPO . |
| WO9413211 | 6/1994 | WIPO . |
| WO9513021 | 5/1995 | WIPO . |

*Primary Examiner*—Michael Powell Buiz
*Assistant Examiner*—Tina T. D. Pham

[57] ABSTRACT

A method and apparatus for closing a punctured blood vessel is described. The method includes providing a clip applier adapted to apply one or more surgical clips to at least a portion of the exterior of a blood vessel in order to close a puncture wound therein. In a preferred embodiment, the clip applier is guided to the puncture by a guide wire and one or more surgical clips are applied to close the puncture wound.

18 Claims, 12 Drawing Sheets

U.S. PATENT DOCUMENTS

| | | |
|---|---|---|
| 5,370,660 | 12/1994 | Weinstein et al. . |
| 5,383,896 | 1/1995 | Gershony et al. . |
| 5,383,897 | 1/1995 | Wholey . |
| 5,383,899 | 1/1995 | Hammerslag . |
| 5,391,182 | 2/1995 | Chin . |
| 5,391,183 | 2/1995 | Janzen et al. . |
| 5,395,319 | 3/1995 | Hirsch et al. . |
| 5,403,278 | 4/1995 | Ernst et al. . |
| 5,411,520 | 5/1995 | Nash et al. . |
| 5,413,571 | 5/1995 | Katsaros et al. . |
| 5,415,657 | 5/1995 | Taymor-Luria . |
| 5,417,699 | 5/1995 | Klein et al. . |
| 5,419,765 | 5/1995 | Weldon et al. . |
| 5,437,292 | 8/1995 | Kipshidze et al. . |
| 5,437,631 | 8/1995 | Janzen . |
| 5,441,517 | 8/1995 | Kensey et al. . |
| 5,443,481 | 8/1995 | Lee . |
| 5,447,502 | 9/1995 | Haaga . |
| 5,447,513 | 9/1995 | Davison et al. ......... 606/143 |
| 5,449,375 | 9/1995 | Vidal et al. . |
| 5,454,833 | 10/1995 | Boussignac et al. . |
| 5,476,469 | 12/1995 | Hathaway et al. . |
| 5,478,326 | 12/1995 | Shiu . |
| 5,478,352 | 12/1995 | Fowler . |
| 5,486,195 | 1/1996 | Myers et al. . |
| 5,507,744 | 4/1996 | Tay et al. . |
| 5,527,319 | 6/1996 | Green et al. ............ 606/143 |
| 5,529,577 | 6/1996 | Hammerslag . |
| 5,540,715 | 7/1996 | Katsaros et al. . |
| 5,545,178 | 8/1996 | Kensey et al. . |
| 5,554,168 | 9/1996 | Petersen . |
| 5,591,204 | 1/1997 | Janzen et al. . |
| 5,591,205 | 1/1997 | Fowler . |
| 5,593,422 | 1/1997 | Van de Moer et al. . |
| 5,601,602 | 2/1997 | Fowler . |
| 5,613,974 | 3/1997 | Andreas et al. . |
| B1 5,275,616 | 1/1996 | Fowler . |

VASCULAR HOLE CLOSURE

BACKGROUND

1. Technical Field

The present disclosure relates to an instrument and method for closing a hole or puncture in a blood vessel. More particularly, this disclosure relates to applying one or more clips to close a hole in a blood vessel after an intravascular catheterization procedure.

2. Background of Related Art

When performing catheterization procedures, such an angiography or angioplasty, a catheter is generally introduced into the vascular system by first penetrating the skin, underlying muscle tissue and blood vessel with a sharpened hollow needle. Next, a guide wire is commonly inserted through the lumen of the hollow needle and is caused to enter the selected blood vessel. Subsequently, the needle is typically stripped off the guide wire and a combination of a dilator and an introducer (or an introducer alone) are fed over the guide wire and pushed through the skin to enter the vessel. The guide wire can then be removed and the desired catheter to carry out the procedure is fed through the lumen of the introducer and advanced through the vascular system until the working end of the catheter is appropriately positioned. Following the conclusion of the catheterization procedure, the working catheter will be withdrawn and, subsequently, the dilator and/or introducer will also be removed from the wound.

At this point in the procedure, the vessel puncture must be sealed in order to stem the flow of blood through the puncture. Because it is common practice to administer a blood thinning agent to the patient prior to many of the catheterization procedures, stemming the blood flow can be troublesome. A common method of healing the wound is to maintain external pressure over the vessel until the puncture naturally seals. This method of puncture closure typically takes about thirty minutes, with the length of time usually being greater if the patient is hypertensive or anti-coagulated. When human hand pressure is utilized, it can be uncomfortable for the patient and can use costly professional time on the part of the hospital staff. Other pressure techniques, such as pressure bandages, sandbags or clamps, have been employed, but these devices also require the patient to remain motionless for, an extended period of time and the patient must be closely monitored to ensure their effectiveness.

Other devices have been disclosed which plug or otherwise provide an obstruction in the area of the puncture. See, for example, U.S. Pat. Nos. 4,852,568 and 4,890,612, wherein a collagen plug is disposed in the blood vessel opening. When the plug is exposed to body fluids, it swells to create a block for the wound in the vessel wall. A potential problem of plugs introduced into the vessel is that particles may break off and float downstream to the point where they may lodge in a smaller vessel, causing an infarct to occur. Collagen material also acts as a nidus for platelet aggregation and, therefore, can cause intraluminal deposition of hemostatic agent, thereby creating the possibility of a thrombosis at the puncture sight. Other plug-like devices are disclosed, for example, in U.S. Pat. Nos. 5,342,393, 5,370, 660 and 5,411,520.

Surgical clips and clip appliers are known have also been used in vascular surgery, particularly to join severed vessels. See, for example, U.S. Pat. No. 4,929,240 (Kirsch, et al). The clips disclosed in the '240 Patent provide an advantage over suturing by decreasing the likelihood of clotting and vascular damage, particularly in micro-vascular repair procedures. While vascular clips have been successfully used in surgery, the surgical procedures in which the clips are used typically allow the surgeon to view the area to be clipped. In catheter puncture repair procedures, however, the wound is generally not visible, making proper clip application, if attempted, difficult.

Therefore, there is a need for surgical techniques suitable for closing punctures in blood vessels, particularly those created during catheterization procedures. This need requires a reliable hemostasis of the puncture in a quick and efficient manner. It would also be advantageous to close the puncture without disposing any foreign substances within the vessel, thereby preventing the likelihood of introducing foreign matter into the circulatory system. The technique also needs to be performed without directly viewing the punctured vessel.

SUMMARY

The present disclosure provides an instrument and method for closing a puncture in a blood vessel by applying at least one surgical clip to at least a portion of the exterior of the vessel. In a preferred embodiment, a guide wire passes extracorporeally through the skin, the vessel puncture, and into the blood vessel. A tubular structure, such as a cannula, is advanced over the guide wire and positioned near or adjacent the exterior of the blood vessel puncture. Next, a surgical clip applier is introduced into the cannula, preferably using the guide wire to guide the clip applier to the puncture sight. Once the distal end of the clip applier is properly positioned adjacent the vessel puncture, one or more surgical clips can be applied to close the puncture. Preferably, at least one clip is applied prior to removing the guide wire and at least one clip is applied subsequent to guide wire removal. After clip application, the clip applier and cannula can be removed and a topical bandage applied.

BRIEF DESCRIPTION OF THE DRAWINGS

Various embodiments are described herein with reference to the drawings, wherein.

DETAILED DESCRIPTION OF THE PREFERRED EMBODIMENTS

Figure 1:
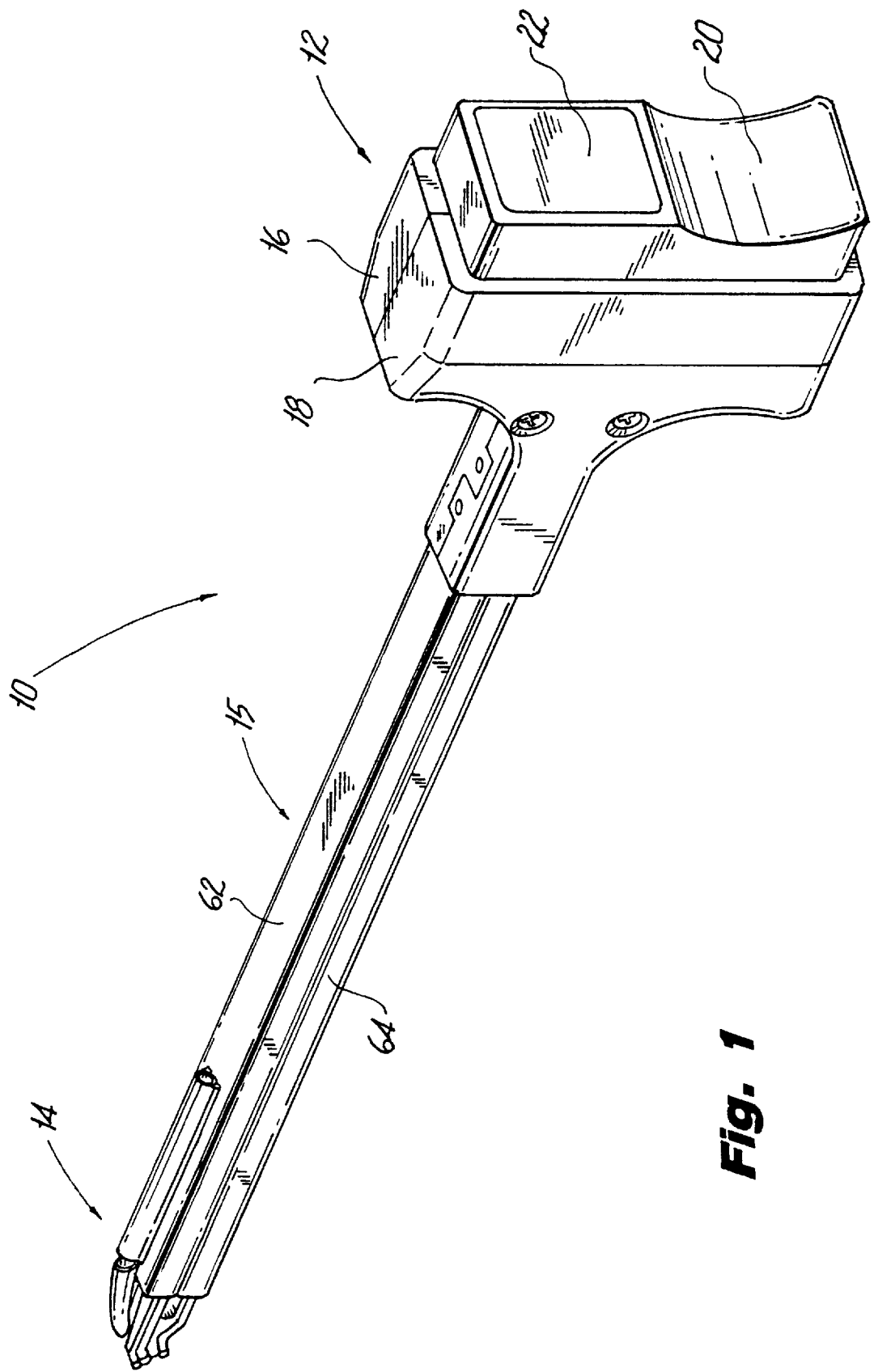
FIG. 1 is a perspective view of a preferred clip applying instrument.
Figure 2:
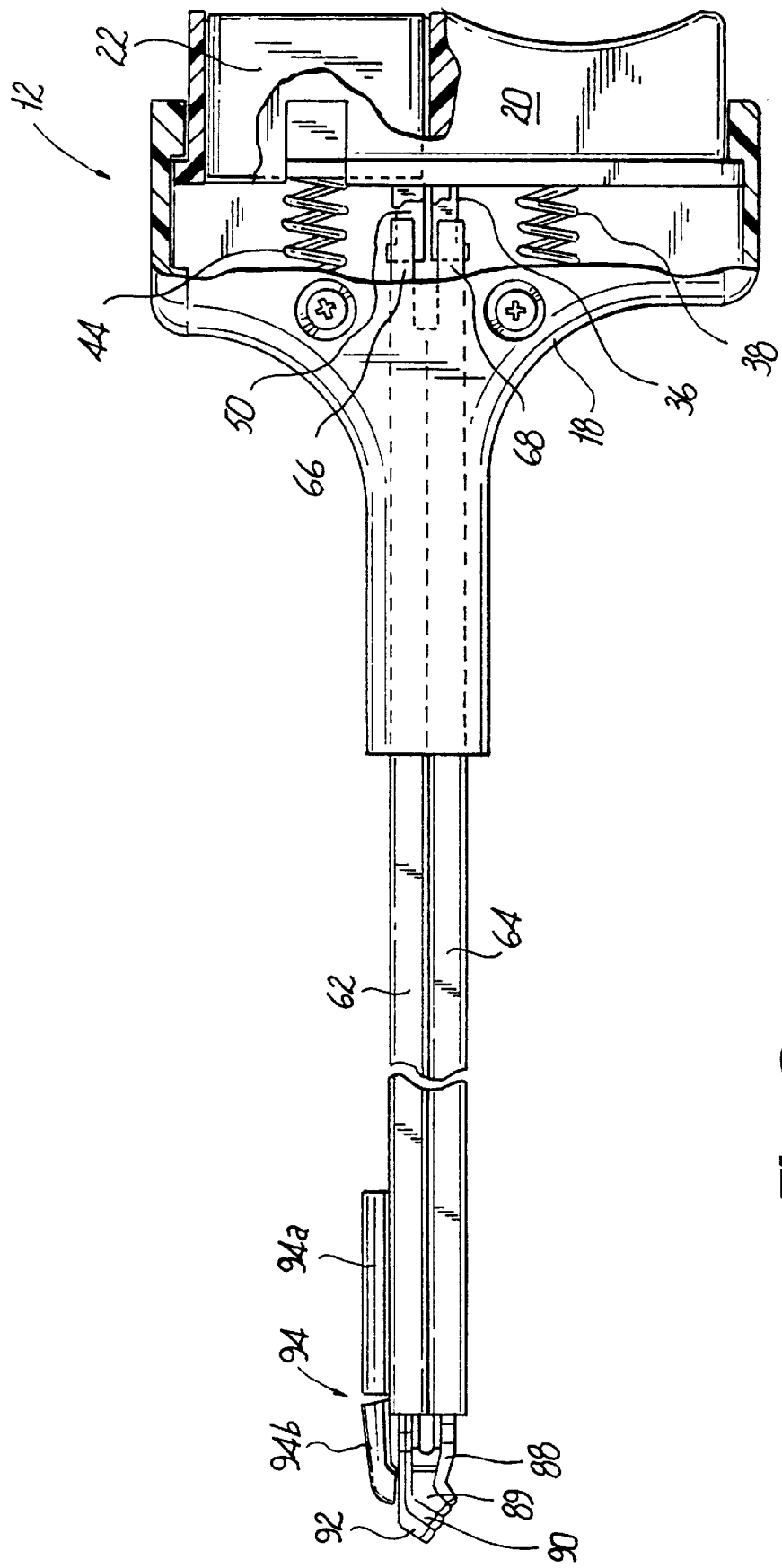
FIG. 2 is a side elevational view in partial cross section of the instrument of FIG. 1.

Referring now in specific detail to the drawings, in which like reference numerals identify similar or identical elements throughout several views, and initially to FIG. 1, a preferred clip applying instrument 10 is shown. Instrument 10 has proximal handle portion 12, distal clip applying portion 14 and intermediate portion 15 disposed therebetween. As used herein, the proximal end of an element is referred to as the end of the element nearest to the surgeon and the distal end of an element is referred to as the element furthest from the surgeon.

Referring to FIGS. 1–3 and 3a, the components of clip applying instrument 10 will be discussed in detail. Handle portion 12 has housing portions 16 and 18 which house primary firing button or actuator 20 and secondary firing button or actuator 22. Primary firing button 20 includes first cavity 24 having side slots 26a and 26b and second cavity 28 having a distally extending projection 30 disposed therein. Projection 30 serves to align and at least partially retain primary button spring 38 between primary firing button 20 and shelf 40, which projects inwardly from housing 18. Structure corresponding to shelf 40 (not shown) can be provided on the inside of housing portion 16 and be positioned to mate with shelf 40 when housing portions 16 and 18 are assembled. Spring 38 biases primary firing button 20 proximally. Also extending distally from button 20 are latching fingers 32a and 32b, each having protrusions 34a and 34b at their respective distal ends, the purpose of which will be discussed below. Between latching fingers 32a and 32b is firing channel engagement member 36.

Secondary firing button 22 has cavity 41 and distally extending projection 42 disposed therein. Projection 42 is similar to projection 30 in the primary firing button and is adapted to engage secondary button spring 44 which is disposed between projection 42 and shelf 46, which projects inwardly from housing 18. Spring 44 biases secondary firing button 22 proximally. Secondary firing button 22 has a pair of distally extending biasing fingers 48a and 48b. Between biasing fingers 48a and 48b is firing channel engagement member 50. Secondary firing button 22 is slidably received within cavity 24 of the primary firing button, wherein side projections 52a and 52b in the secondary button are slidably received in slots 26a and 26b of the primary button. Because button 20 can move relative to button 22, the distal clip applying structures are independently actuable, as will be discussed in greater detail, below. When handle portion 12 is assembled, firing buttons 20 and 22 are nested between housing portions 16 and 18 and screws 54 and 56 serve to at least partially secure the assembly. Of course other means for securing the housing portions can be utilized, such as, for example, glue, welds, friction fittings and the like.

Firing buttons 20 and 22, as best shown in FIG. 1, are positioned on the proximal most portion of the apparatus for accessibility to the user. To enable the user to readily differentiate between the buttons, primary firing button 20 has concave surface and secondary firing button 22 has a substantially planar outer surface. Each of the buttons are configured to be pressed inwardly towards housing portions 16, 18 to fire the clips in the manner discussed below. Clearly, other actuator configurations in alternate locations are contemplated. For example, instead of having two firing buttons, a single firing button having different stages of firing along a common stroke path tan be used. Also, for example, trigger mechanisms or gas-powered mechanisms can be provided as is known in the art.

Turning to the intermediate and distal portions of instrument 10, there are preferably two firing channels 62 and 64 which house clip bars 66 and 68, respectively. The proximal end portions of the firing channels have windows 70 and 72 which are configured to receive the distal ends of firing channel engagement members 36 and 50. Jaws 88 extend distally from clip bar 68 while jaws 90 and 92 extend distally from clip bar 66. When the clip bars are assembled within the firing channels, each set of jaws are disposed distal of the firing channel distal ends. Therefore, by depressing the firing buttons and causing the firing channels to move distally, the jaws are cammed inwardly, resulting in clip closure (discussed in greater detail below). The firing channels also have intermediate slots 74 and 76 which permit the channels to slide relative to pins 58 and 60 during operation. Clip bars 66 and 68 have apertures 78, 80, 82 and 84 to receive pins 58 and 60 therethrough to thereby mount the bars 66, 68 to housing portions 16, 18. During operation, pins 58 and 60 prevent distal/proximal movement of the clip bars while firing channels 62 and 64 slide thereover to fire clips. In the particular preferred embodiment shown in FIG. 3a, the distal end of clip bar 68 has a single pair of jaws 88 configured to retain and apply one surgical clip, while the distal end of clip bar 66 has two pairs of jaws, 90 and 92, each configured to retain and apply a surgical clip. Jaw 92, as shown, is preferably positioned on top of jaw 90 while jaw spacer 89 is provided to separate jaws 88 from jaws 90 and 92. Jaws 88, 90 and 92 are preferably disposed at a common angle with respect to the longitudinal axis of clip applier 10.

Figure 3:
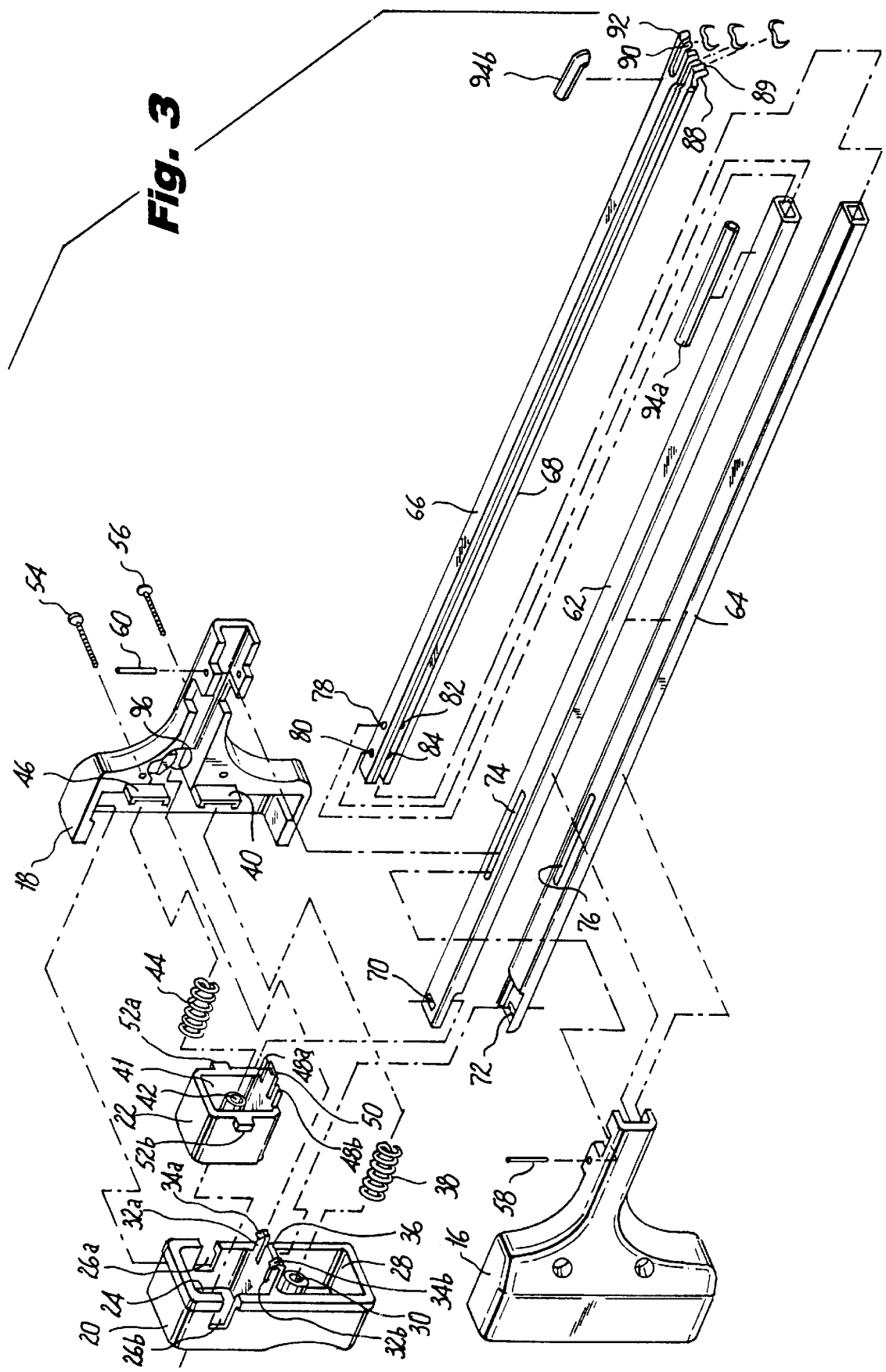
FIG. 3 is an exploded perspective view of the instrument of FIG. 1.
Figure 3A:
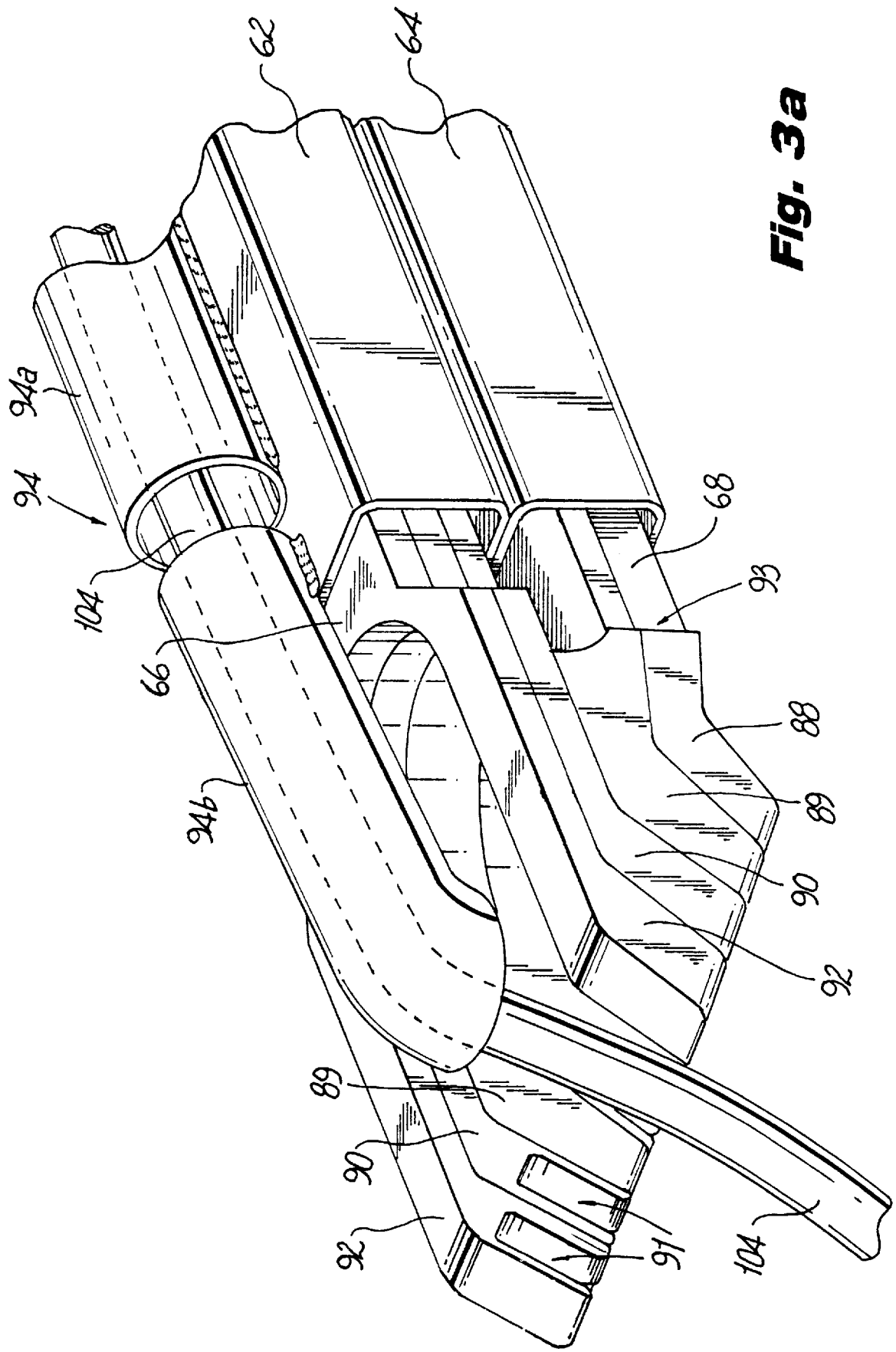
FIG. 3a is an enlarged perspective view of the distal, clip applying portion of the instrument of FIG. 1.

FIG. 3a also illustrates the distal end of firing channel 62 having tubular guide wire guide member 94 secured thereto. Guide member 94 is configured to receive a guidewire to facilitate placement of the instrument at the desired surgical site and is preferably a hollow structure constructed from one or more pieces. In the drawings, guide member 94 is shown in two parts, part 94a being disposed along the firing channel and part 94b being positioned to over hang the jaw structure. Guide member 94 is preferably secured by welding, however, other suitable securement methods can be used. The function of guide 94 is discussed in greater detail below.

Figure 3B:
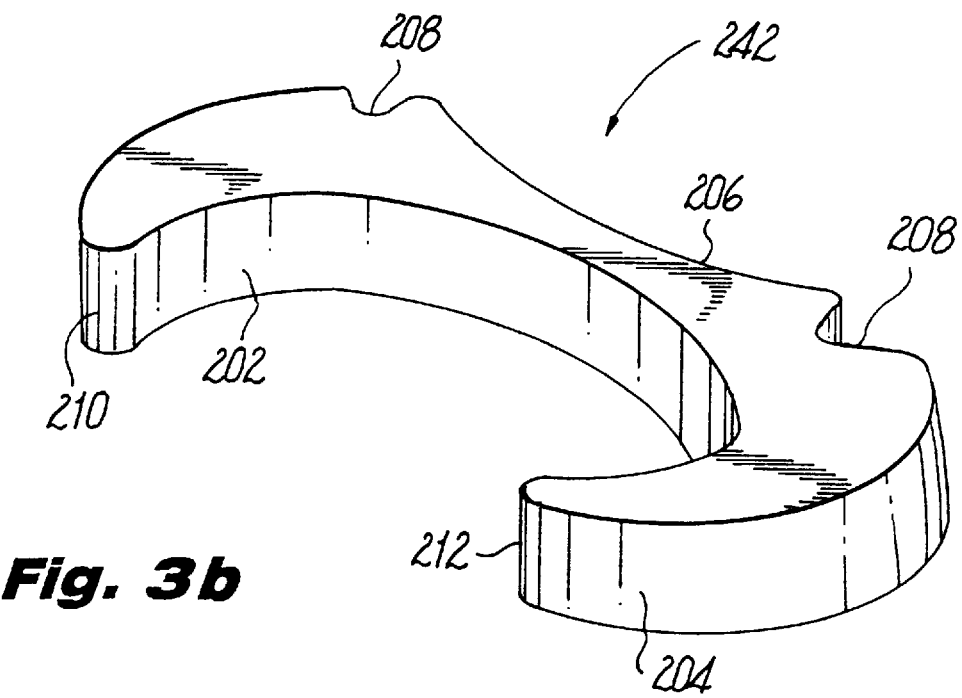
FIG. 3b is an enlarged perspective view of a clip suitable for use with the disclosed clip applier.
Figure 3C:
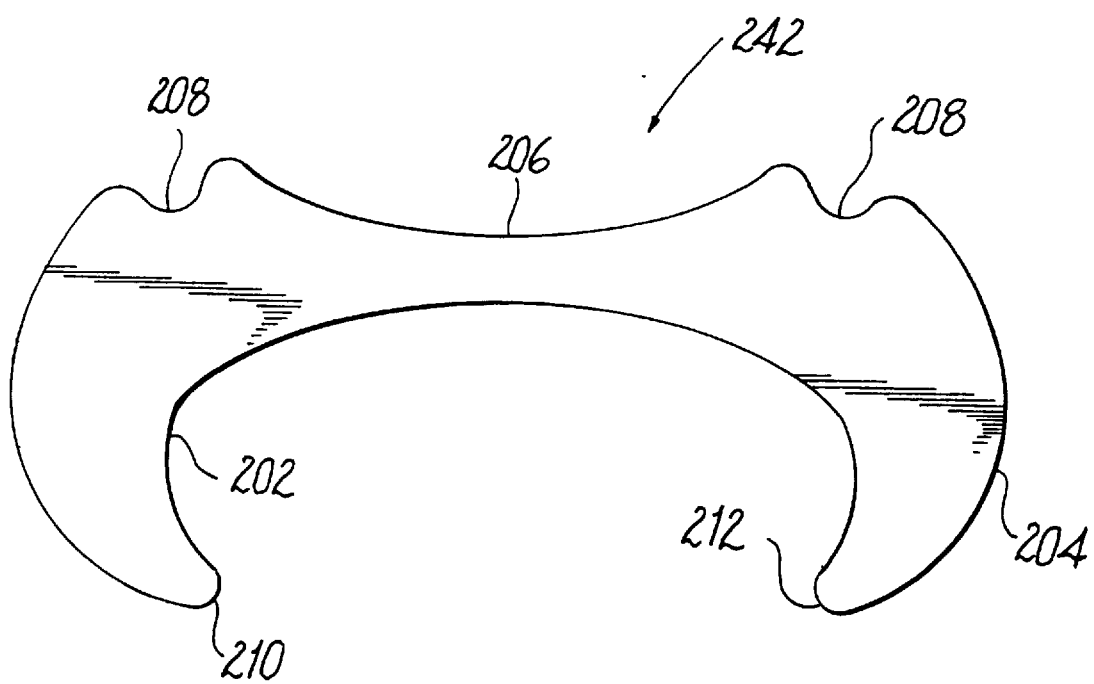
FIG. 3c is a side elevational view of the clip of FIG. 3b.
Figure 4:
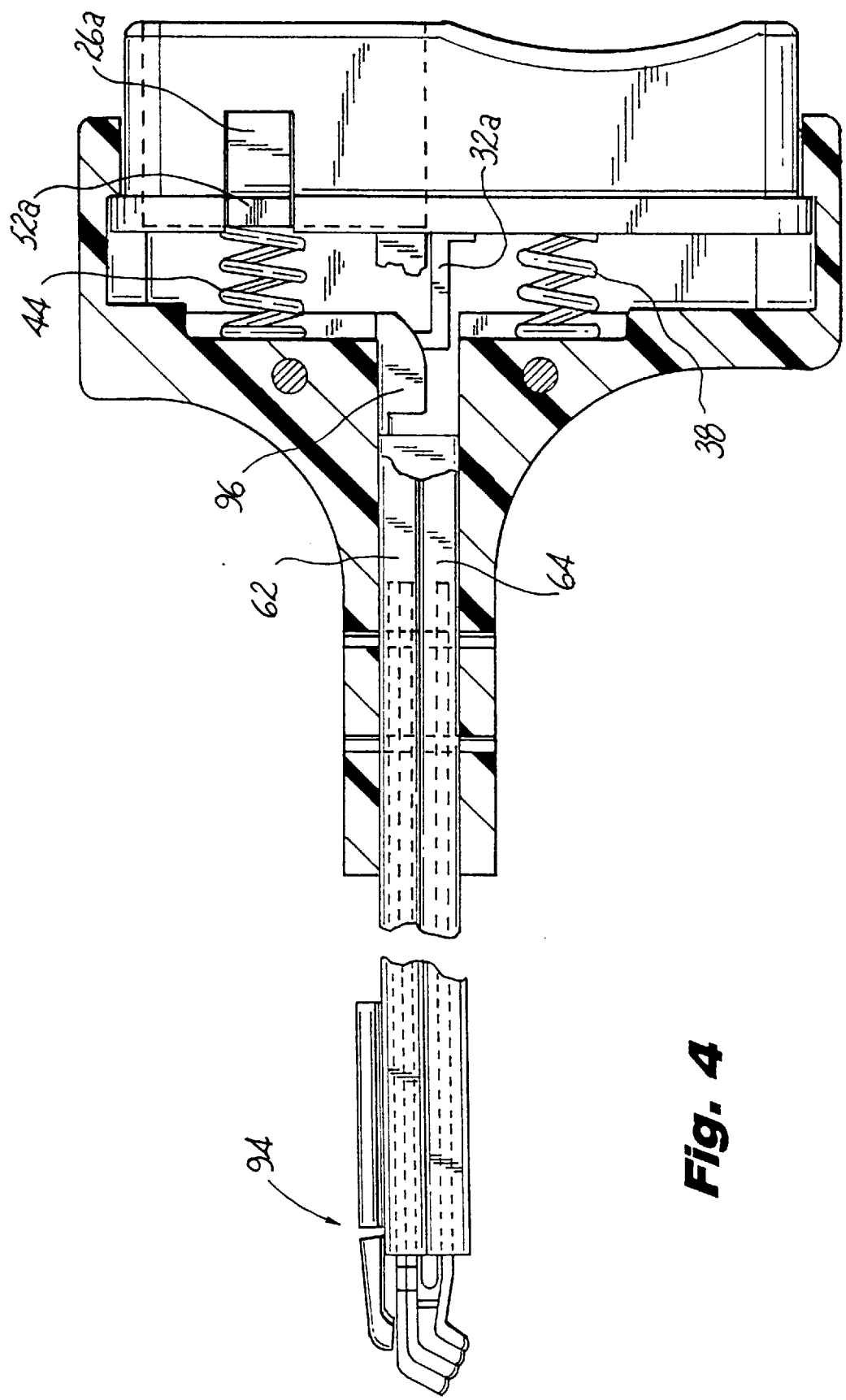
FIG. 4 is a side elevational view in partial cross section of the instrument of FIG. 1 prior to actuation.

A preferred clip is shown in FIGS. 3b and 3c. Surgical clip 242 is designed for application by clip applier 10 and is formed of a unitary piece of biologically acceptable, plastically deformable material such as a noble metal (i.e., gold, silver, platinum, titanium, etc.). While metal clips are presently preferred, it is contemplated that other materials, such as suitable polymer plastics, can be used. The material, preferably titanium, is sufficiently ductile or plastically deformable so that when the clip is crimped, there is minimal spring-back. The clip is designed to apply constant force to tissue, regardless of tissue thickness, without penetration. However, clips that penetrate tissue can also be utilized.

Clip 242 includes a pair of inwardly curved arms 202 and 204 interconnected by a bridge portion 206. The two arms extend generally perpendicular to bridge portion 206 and terminate at tips 210 and 212 which are rounded to prevent injury to the subject tissue. The bridge portion 206 includes a pair of optional grooves 208 which are useful for receiving an advancing/pushing bar if an array of clips are to be stored and sequentially applied. Clip slots 91 (FIG. 3a) in jaws 88, 90 and 92 are configured to receive arms 202 and 204 of clips 242. The clip can be sized according to the particular end use, but it is generally a size suitable for micro-surgical applications in both non-endoscopic and endoscopic procedures.

Figure 5:
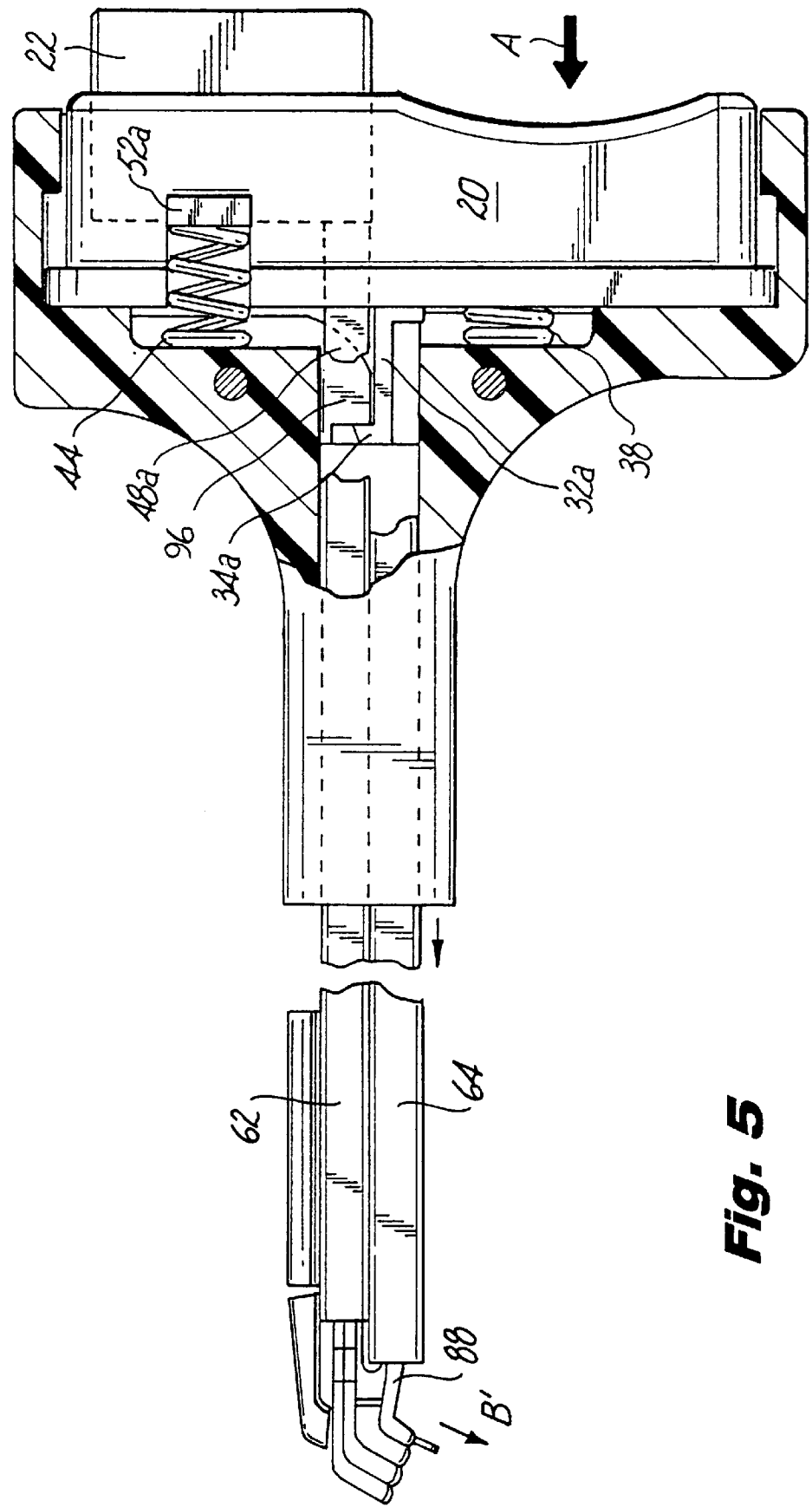
FIG. 5 is a side elevational view in partial cross section of the instrument of FIG. 1 after actuation of the primary firing button.
Figure 6:
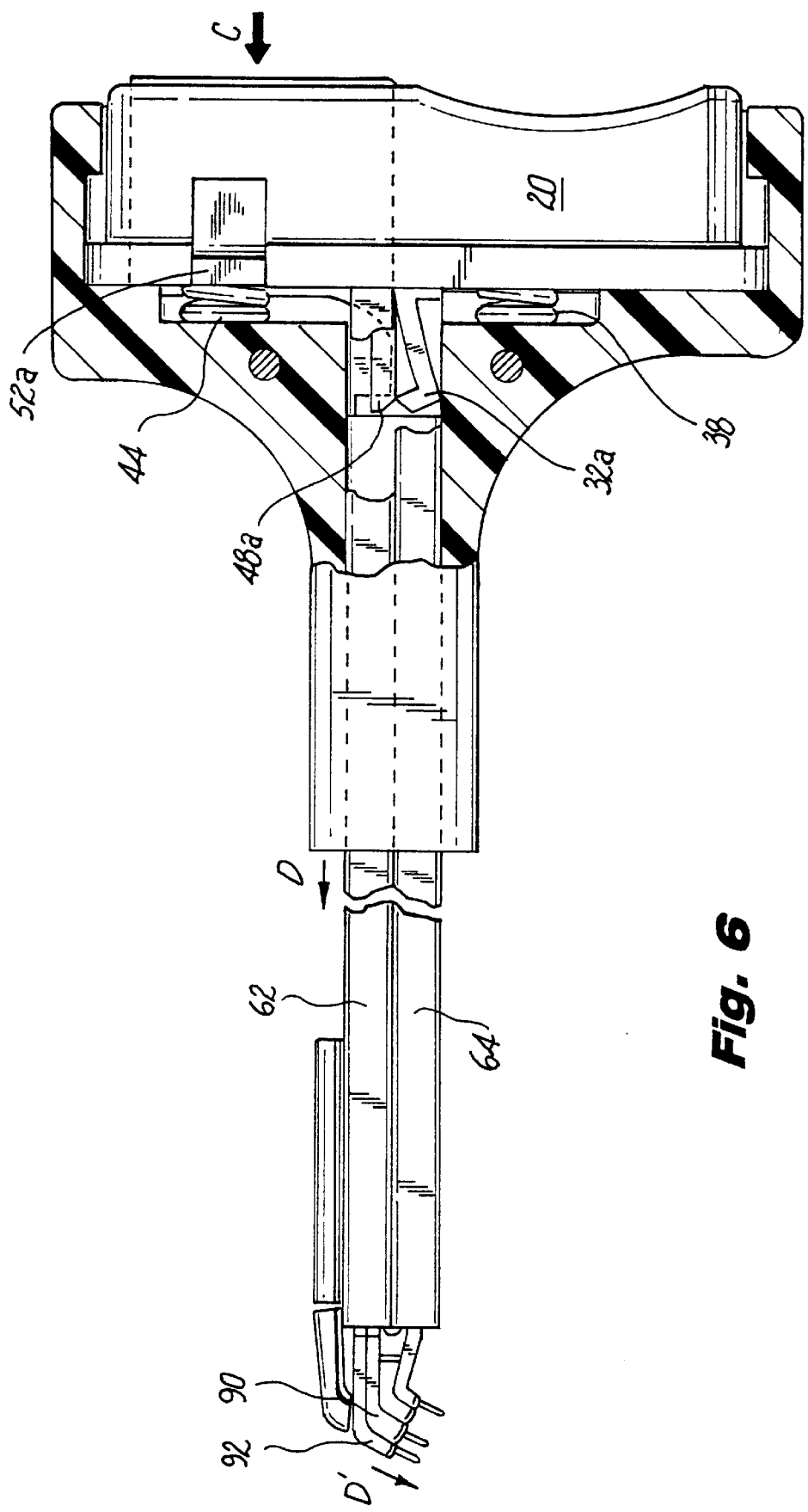
FIG. 6 is a side elevational view in partial cross section of the instrument of FIG. 1 after actuation of the secondary firing button.
Figure 7:
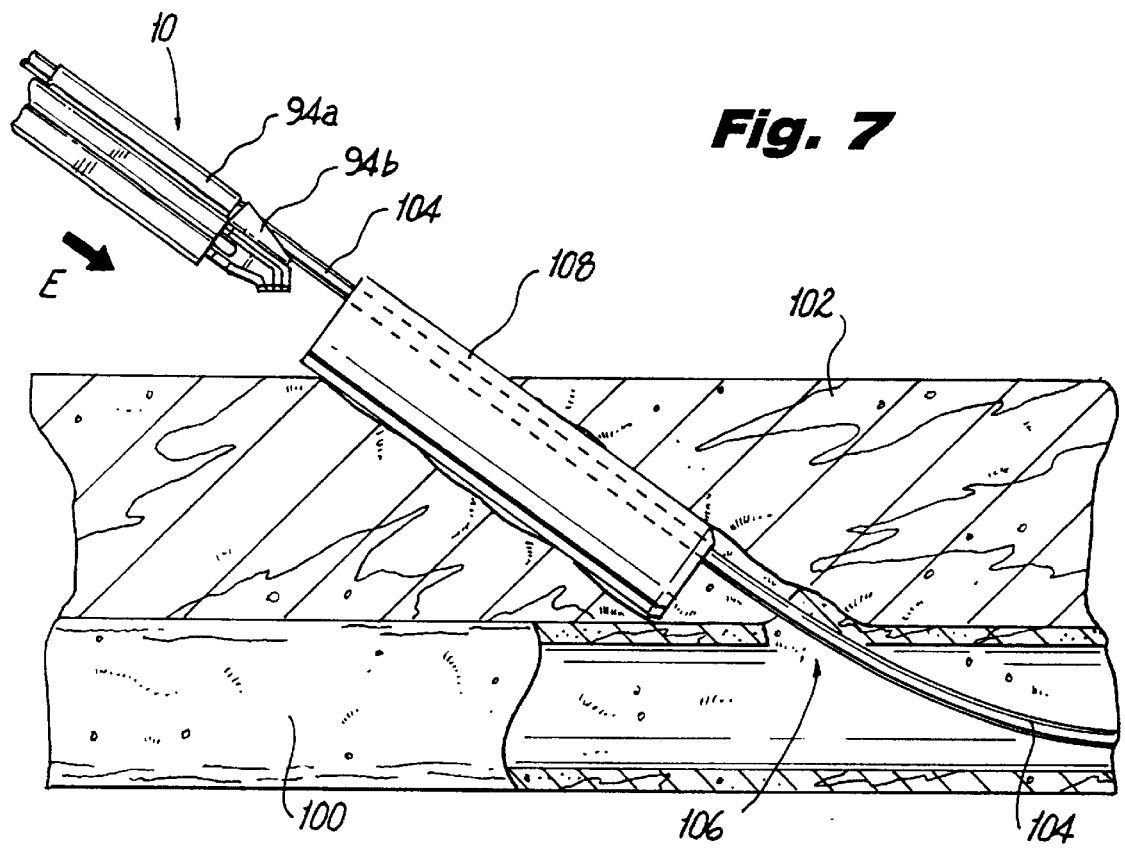
FIG. 7 is a side elevational view in partial cross-section showing the instrument of FIG. 1 being advanced towards a cannula using a guide wire as a guide.
Figure 8:
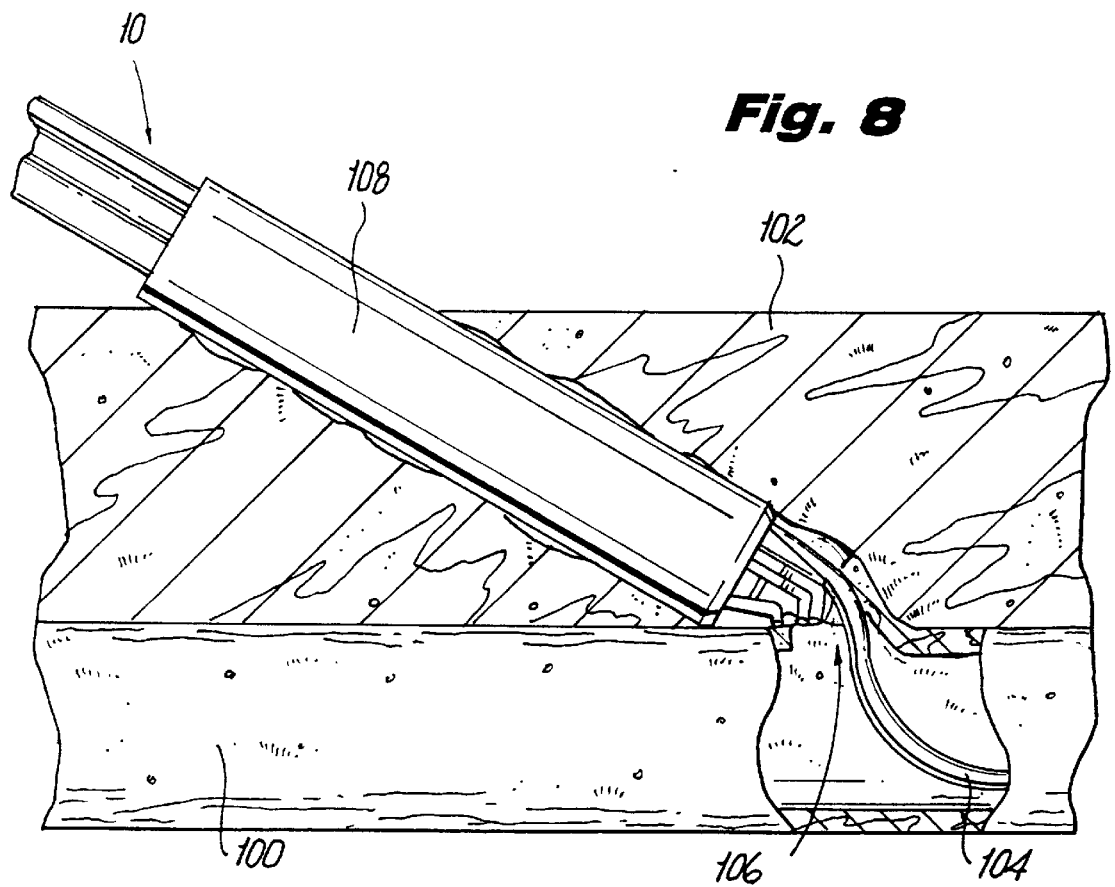
FIG. 8 is a side elevational view in partial cross-section showing the distal end of the instrument of FIG. 1 disposed adjacent a blood vessel to be clipped.
Figure 9:
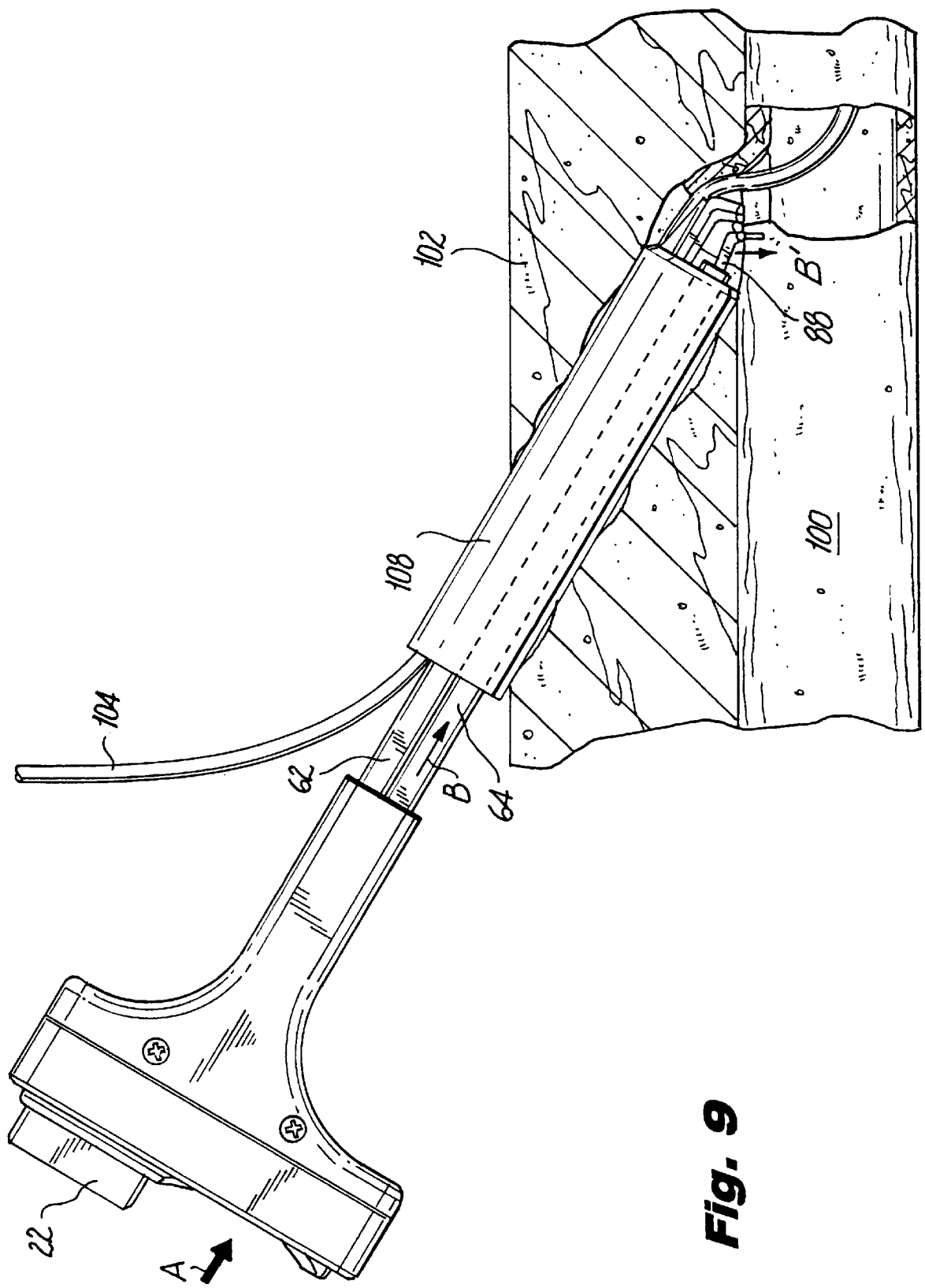
FIG. 9 is a side elevational view in partial cross-section, showing the instrument of FIG. 1 applying one clip to a portion of the exterior of a blood vessel.
Figure 10:
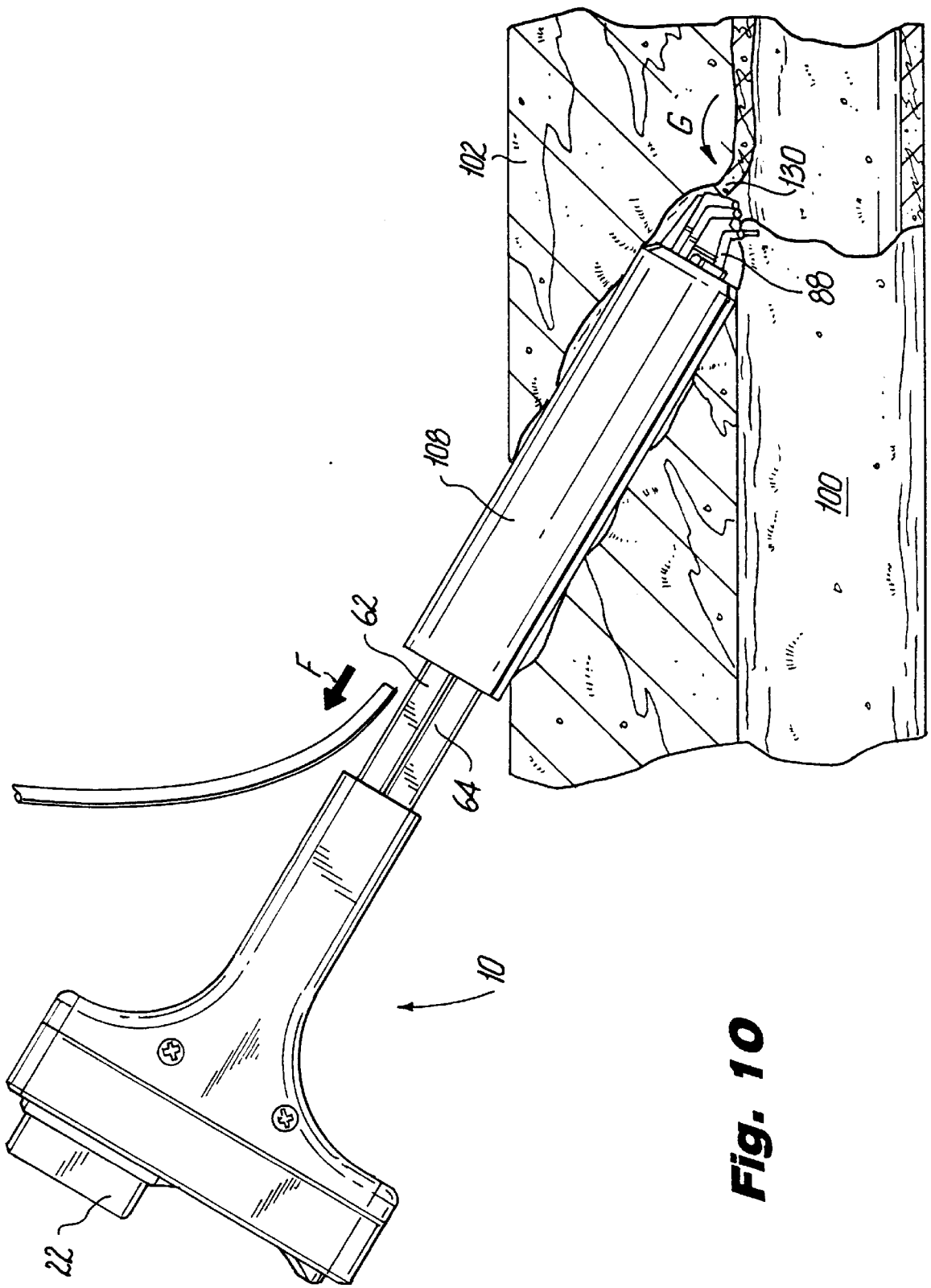
FIG. 10 is a side elevational view in partial cross-section showing the removal of the guide wire prior to application of additional surgical clips.
Figure 12:
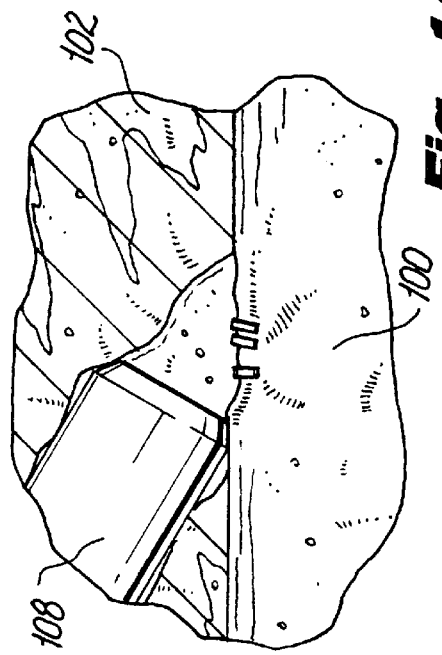
FIG. 12 is a side elevational view in partial cross-section showing the clipped blood vessel after the clip applier of FIG. 1 has been fired and withdrawn from the cannula.
Figure 11:
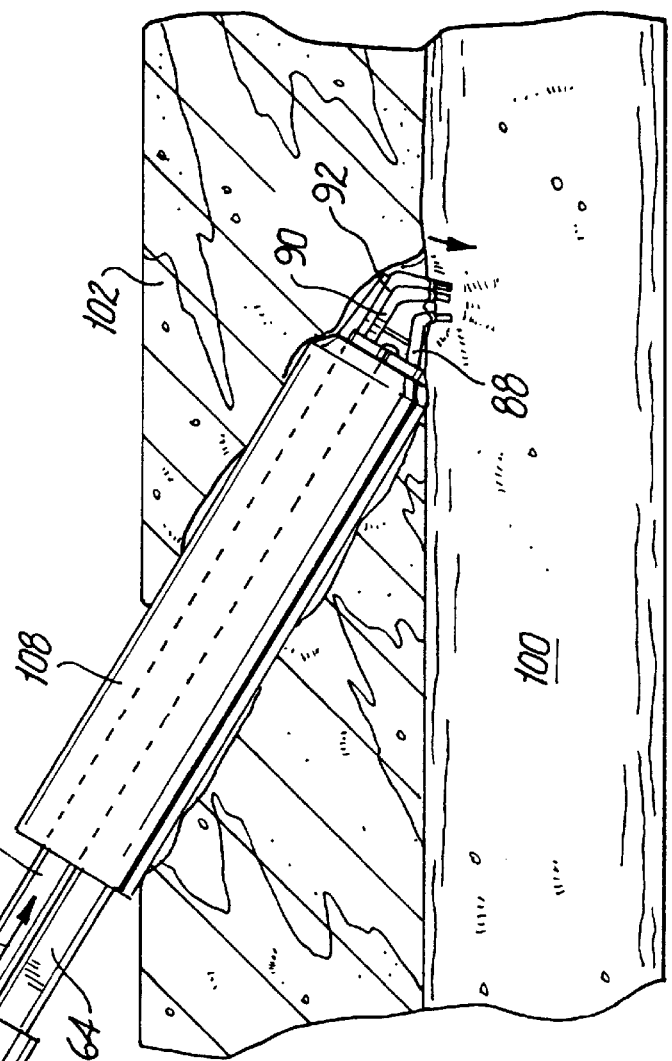
FIG. 11 is a side elevational view in partial cross-section showing two clips being applied substantially simultaneously to the blood vessel.
Figure 11:
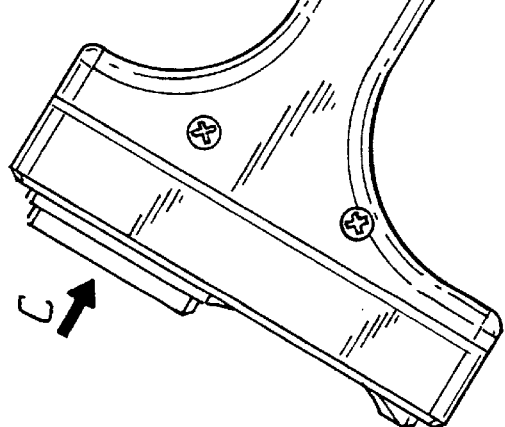

The operation of instrument 10 is generally shown in FIGS. 5–11. As shown in FIGS. 5 and 9, the first clip is applied by depressing primary firing button 20, in the direction of Arrow A. Depression of button 20 causes firing channel 64 to slide distally (Arrow B) over stationary clip bar 68 (FIG. 3), causing jaws 88 to cam inwardly as the distal end of channel 64 contacts camming surface 93 of the jaws (FIG. 3a). As the jaws cam inwardly, clip held therein (Arrow B') is formed. As shown in FIG. 5, secondary firing button 22 remains stationary as primary firing button 20 is depressed. When button 20 is completely depressed, protrusions 34a and 34b of latching fingers 32a and 32b catch on ledge member 96 in handle portion 12. When latched, button 20 and firing channel 64 are held in the distal position, thereby maintaining jaws 88 in the closed position. Turning to FIGS. 6 and 11, jaws 90 and 92 are closed by depressing secondary firing button 22 (Arrow C) which causes firing channel to move distally (Arrow D) over stationary clip bar 66, further causing both jaws 90 and 92 to form the clips held therein (Arrow D'). At the distal end of travel of button 22, biasing fingers 48a and 48b contact latching fingers 32a and 32b and release the fingers from ledge 96, thereby freeing button 20. Upon release of pressure from button 22, springs 38 and 44 bias buttons 20 and 22, respectively, in the proximal direction. Proximal movement of the buttons also cause firing channels 62 and 64 to move proximally. With the firing channels in the proximal position, jaws 88, 90 and 92 resiliently spring open to release the deformed clips.

A preferred method of closing a hole in a blood vessel is shown in FIGS. 7–11. Initially referring to FIG. 7, a blood vessel or artery 100, such as the femoral artery, is shown disposed below skin 102 of a patient. Vessel 100 is shown subsequent to a catheterization procedure, i.e., a puncture 106 has been created in vessel 100. Guide wire 104 passes through skin 102 and enters artery 100 at puncture sight 106. If the guide wire was removed during the catherization procedure, it is preferably reinserted to perform the clipping procedure. Other structures for aiding in locating the clip applier, however, can be used. Shown in FIG. 7 is tube or cannula 108 disposed in skin layer 102 and abutting vessel 100. Cannula 108 aids in accessing vessel 100. Arrow E depicts clip applier 10 being advanced through cannula 108 in a distal direction, towards puncture sight 106. To aid in locating the distal clip applying portion of instrument 10 adjacent the vessel puncture, guide members 94a and 94b receive guide wire 104 therethrough. In FIG. 8, the distal portion of cannula 108 is at least partially disposed adjacent vessel 100 and clip applier 10 has been advanced so that the distal end 14 is disposed in a desired orientation adjacent puncture 106.

After the distal end of clip applier 10 is positioned adjacent the wound sight, a first clip is applied from jaws 88 by depressing primary firing button 20 in the direction of Arrow A (FIG. 9). As previously described, when button 20 is completely depressed, button 20 and firing channel 64 are held in the distal position, thereby maintaining jaws 88 in the closed position.

At this point in the procedure, with reference to FIG. 10, guide wire 104 can be removed (Arrow F) from the surgical site. Because jaws 88 are closed and maintain clamping pressure on vessel 100, the orientation of clip applier 10 and vessel 100 is generally maintained and the guide wire is no longer necessary for alignment. Removal of guide wire 104 allows the vessel to further naturally close. For example, flap 130 in blood vessel 100 is no longer biased away from the vessel wall by guide wire 104 and, therefore, flap 130 can advantageously shift to a position more suitable to closure by jaws 90 and 92. As shown in FIG. 11, second and third clips can now be applied substantially simultaneously by jaws 90 and 92, thereby completing the hole closure procedure, by depressing button 22 as described above. The clips are placed adjacent the first clip applied by jaws 88. Upon release of button 22, both buttons 20 and 22 move proximally, thereby allowing jaws 88, 90 and 92 to open and release the clips and vessel. Subsequent to the application of the clips, clip applier 10 and cannula 108 can be removed from the surgical site. A topical bandage or other structure can then be applied to the exterior of skin 102, if desired.

It is contemplated that the present method and device can be used not only with catheterization procedures but other medical procedures where it is desirable to seal an incision or puncture in patient's blood vessel or artery. By using surgical clips as set forth in the present disclosure, the need to apply pressure to the wound site for an extended period of time is unnecessary. In addition, because the clip or clips are applied externally to the vessel, the danger of foreign matter entering the circulatory system is essentially eliminated.

It will be understood that various modifications can be made to the embodiments disclosed herein. For example, while the application of three clips has been described as a preferred embodiment, a single clip or any combination of clips can be applied. Such clips can be applied simultaneously or sequentially. It is also contemplated that the order of applying clips and withdrawing the guide wire can be modified. For example, the distal end of the clip applier can be disposed adjacent the vessel and the guide wire can be removed prior to the application of any clips. Also, it is contemplated that each clip or clips to be applied can be affixed to the vessel prior to removal of the guide wire. Cannula or tube 108 is also optional to the procedure, but is useful for aiding in the insertion and withdrawal of the clip applier. It is also possible to properly position the clip applier without the use of a guidewire. However, some structure to aid in locating the distal end of the instrument is preferred. In addition, the clip applier and method described herein could be modified by one skilled in the art to be used endoscopically. Therefore, the above description should not be construed as limiting but merely as examples of preferred embodiments. Those skilled in the art will envision other modifications within the scope and spirit of the claims appended hereto.

What is claimed is:

1. A method of closing a puncture in a blood vessel comprising:

inserting a guide wire into a blood vessel;

providing a clip applier adapted to apply at least one surgical clip;

using the guide wire to guide a portion of the clip applier to a position substantially adjacent the puncture wound in the blood vessel; and applying at least one surgical clip to the blood vessel.

2. The method according to claim 1, further comprising the step of providing a cannula and wherein the step of inserting the clip applier includes passing the clip applier through the cannula structure.

3. The method according to claim 1, wherein the clip applier is adapted to apply at least two surgical clips and the step of applying comprises applying at least two surgical clips.

4. The method according to claim 1, further comprising the step of providing the clip applier with a tubular structure secured thereto, the tubular structure being adapted to receive the guide wire, wherein the step of guiding the clip applier to the puncture wound includes sliding the clip applier relative to the guide wire, using the tubular structure as a guide.

5. The method according to claim 1, further comprising the step of removing the guide wire subsequent to applying at least one surgical clip.

6. The method according to claim 5, further comprising the step of applying a second surgical clip subsequent to removing the guide wire.

7. The method according to claim 1, wherein the clip applier is adapted to apply at least two surgical clips and has first and second pairs of jaws wherein the step of applying the surgical clips includes the steps of:

securing a first clip to the blood vessel by closing the first pair of jaws to deform the clip;

maintaining the first pair of jaws in the closed position;

closing a surgical clip with the second pair of jaws while the first jaws remain in the closed position.

8. The method according to claim 7, wherein subsequent to the closure of the second clip, the first pair of jaws are caused to move to an open position.

9. The method according to claim 7, wherein the guide wire is removed subsequent to the application of the first clip and prior to the application of the second clip.

10. In a surgical method including the steps of;

providing a guidewire, providing a catheter, creating a passageway through the skin and underlying tissue of a patient to gain access to a desired vessel of the patient, creating a puncture in the vessel of the patient, inserting the guidewire through the passageway and the puncture in the patient's vessel, inserting the catheter through the passageway and the puncture in the patient's vessel, and removing the inserted portion of the catheter from the patient, the improvement comprising:

providing a cannula having proximal and distal end portions; inserting the distal end portion of the cannula through the passageway and into general abutment with the vessel to provide an access channel to the vessel puncture; providing a surgical clip applier;

inserting the surgical clip applier through the cannula while using the guidewire to direct a distal end of the clip applier to the vessel puncture; and applying at least one surgical clip to the patient's vessel to at least partially close the vessel puncture through which the catheter was inserted.

11. In a surgical method including the steps of;

creating a passageway through the skin and underlying tissue of a patient to gain access to a desired vessel of the patient, creating a puncture in the vessel of the patient and performing a surgical procedure, the improvement comprising:

providing a guidewire;

providing a cannula having proximal and distal end portions;

inserting the guidewire into the passageway and through the vessel puncture;

inserting the distal end portion of the cannula through the passageway and into general abutment with the vessel to provide an access channel to the vessel puncture;

providing a surgical clip applier;

inserting the surgical clip applier through the cannula while using the guidewire to direct a distal end of the clip applier to the vessel puncture; and applying at least one surgical clip to the patient's vessel to at least partially close the vessel puncture.

12. A surgical instrument comprising a handle portion, an intermediate portion and first and second pairs of jaws at a distal end of the intermediate portion, each of the first and second pairs of jaws having a surgical clip disposed between each said pairs of jaws, the jaws having movable portions for deforming the surgical clips, wherein the first pair of jaws is independently actuable from the second pair of jaws.

13. The surgical instrument according to claim 12, wherein at least one of the pairs of jaws is actuated by a push button.

14. A surgical instrument having proximal and distal end portions comprising:

at least one pair of jaws at a distal end thereof, the jaws being movable from a first position to a second position wherein the jaws are closer to each other in the second position, the jaws being adapted to apply at least one surgical clip;

at least one surgical clip disposed between the at least one pair of jaws; and a guide tube secured to a distal portion of the instrument.

15. A method of closing a puncture in a blood vessel comprising:

inserting a guide wire into a blood vessel;

providing a clip applier adapted to apply at least one surgical clip;

providing the clip applier with a tubular structure secured thereto, the tubular structure being adapted to receive the guide wire;

using the guide wire to guide a portion of the clip applier to a position substantially adjacent the puncture wound in the blood vessel by sliding the clip applier relative to the guide wire and using the tubular structure as a guide; and applying at least one surgical clip to the blood vessel.

16. A method of closing a puncture in a blood vessel comprising:

inserting a guide wire into a blood vessel;

providing a clip applier adapted to apply at least one surgical clip;

using the guide wire to guide a portion of the clip applier to a position substantially adjacent the puncture wound in the blood vessel;

applying at least one surgical clip to the blood vessel; and removing the guide wire subsequent to applying at least one surgical clip.

17. A method of closing a puncture in a blood vessel comprising:

inserting a guide wire into a blood vessel;

providing a clip applier adapted to apply at least two surgical clips and having first and second pairs of jaws;

using the guide wire to guide a portion of the clip applier to a position substantially adjacent the puncture wound in the blood vessel; and securing a first clip to the blood vessel by closing the first pair of jaws to deform the clip;

maintaining the first pair of jaws in the closed position;

closing a surgical clip with the second pair of jaws while the first jaws remain in the closed position.

18. A surgical instrument comprising a handle portion, an intermediate portion and first and second pairs of jaws at a distal end of the intermediate portion, each of the first and second pairs of jaws having movable portions for deforming at least one surgical clip, wherein the first pair of jaws is independently actuable from the second pair of jaws and at least one of the pairs of jaws is actuated by a push button.

* * * * *